United States Patent
Nakamura et al.

(10) Patent No.: US 9,888,987 B2
(45) Date of Patent: Feb. 13, 2018

(54) DENTAL BLANK TO BE MACHINED, METAL POWDER FOR POWDER METALLURGY, DENTAL METAL FRAME FOR PORCELAIN BONDING, AND DENTAL PROSTHESIS

(71) Applicant: Seiko Epson Corporation, Tokyo (JP)

(72) Inventors: Hidefumi Nakamura, Hachinohe (JP); Yukihiko Shiohara, Hachinohe (JP)

(73) Assignee: Seiko Epson Corporation (JP)

( * ) Notice: Subject to any disclaimer, the term of this patent is extended or adjusted under 35 U.S.C. 154(b) by 300 days.

(21) Appl. No.: 14/497,792

(22) Filed: Sep. 26, 2014

(65) Prior Publication Data
US 2015/0093721 A1 Apr. 2, 2015

(30) Foreign Application Priority Data

Sep. 27, 2013 (JP) .................................. 2013-202722
Aug. 20, 2014 (JP) .................................. 2014-167734

(51) Int. Cl.
*A61C 13/00* (2006.01)
*A61C 13/083* (2006.01)
*C22C 19/07* (2006.01)

(52) U.S. Cl.
CPC ...... *A61C 13/0022* (2013.01); *A61C 13/0835* (2013.01); *C22C 19/07* (2013.01)

(58) Field of Classification Search
CPC . A61C 13/00; A61C 13/0022; A61C 13/0835; A61C 19/07; B22F 3/22; B22F 3/12; B22F 1/00; B22F 3/24
See application file for complete search history.

(56) References Cited

U.S. PATENT DOCUMENTS

| | | | |
|---|---|---|---|
| 3,865,585 A | 2/1975 | Rademacher | |
| 4,116,724 A | 9/1978 | Hirschfeld et al. | |
| 2008/0232998 A1* | 9/2008 | Prasad | A61C 13/0003 420/436 |
| 2011/0275031 A1* | 11/2011 | Jana | A61C 13/0006 433/172 |

(Continued)

FOREIGN PATENT DOCUMENTS

| | | |
|---|---|---|
| GB | 943190 A | 12/1963 |
| JP | 11-001738 | 1/1999 |

(Continued)

OTHER PUBLICATIONS

Extended European Search Report for Application No. EP 14 18 6699 dated Feb. 27, 2015 (6 pages).

*Primary Examiner* — Nicholas Lucchesi
(74) *Attorney, Agent, or Firm* — Harness, Dickey & Pierce, P.L.C.

(57) ABSTRACT

A dental blank is provided for yielding a metal frame having a desired shape according to a dental CAD/CAM system and a machining process. The dental blank is formed from a metal powder sintered body and contains Co as a main component, Cr in a proportion of 26% by mass or more and 35% by mass or less, Mo in a proportion of 5% by mass or more and 12% by mass or less, and Si in a proportion of 0.5% by mass or more and 1.0% by mass or less. Further, part of the Si is silicon oxide, and the ratio of the silicon oxide to the total amount of Si is preferably 10% by mass or more and 90% by mass or less.

9 Claims, 7 Drawing Sheets

(56) References Cited

U.S. PATENT DOCUMENTS

| | | |
|---|---|---|
| 2011/0314965 A1 | 12/2011 | Nakamura |
| 2012/0114516 A1 | 5/2012 | Hachenberg et al. |
| 2012/0174404 A1* | 7/2012 | Wolz ................. A61C 13/0003 29/896.1 |
| 2012/0244035 A1* | 9/2012 | Cascone ................. C22C 30/00 420/583 |
| 2013/0224688 A1* | 8/2013 | Mayr ....................... A61C 5/10 433/200.1 |

FOREIGN PATENT DOCUMENTS

| | | |
|---|---|---|
| JP | 2007-215854 A | 8/2007 |
| JP | 2009-138259 A | 6/2009 |
| JP | 2012-007205 A | 1/2012 |
| JP | 2012-087415 A | 5/2012 |
| JP | 2012-087416 A | 5/2012 |

\* cited by examiner

DENTAL BLANK TO BE MACHINED, METAL POWDER FOR POWDER METALLURGY, DENTAL METAL FRAME FOR PORCELAIN BONDING, AND DENTAL PROSTHESIS

BACKGROUND

1. Technical Field

The present invention relates to a dental blank to be machined, a metal powder for powder metallurgy, a dental metal frame for porcelain bonding, and a dental prosthesis.

2. Related Art

In the prosthesis of a missing part of a tooth crown or a missing tooth in a dental treatment, a crown, a bridge, or a denture is used in many cases. Among these, from the viewpoint of aesthetic appearance and functionality, a dental prosthesis obtained by bonding a ceramic material called "porcelain" to the surface of a metal frame is used.

JP-A-11-1738 discloses an alloy for a noble metal-based metal frame obtained by adding a metal element such as Sn, Ga, or In to a metal element such as Au, Pd, Cu, Ir, or Ag. This alloy can be molded into a desired shape by casting, and therefore, by bonding porcelain for tooth crown restoration to the surface of a metal frame formed from this alloy, a dental prosthesis having excellent aesthetic appearance can be obtained.

On the other hand, recently, a method for forming a metal frame based on shape data obtained by measuring the three-dimensional shape of an affected part is getting popularized. Such a mechanism is called "dental CAD/CAM system". The CAD (computer aided design) is a system that acquires the three-dimensional shape data of an affected part with a 3D scanner or the like and digitizes the data. Further, the CAM (computer aided manufacturing) is a system that cuts out a metal frame having a shape suited to the affected part by machining a workpiece based on the digitized data generated by the CAD. The dental CAD/CAM system combining these systems can easily achieve high dimensional accuracy which had to rely on the skill of dental technicians in the past, and therefore is expected to be further popularized because it can efficiently form a metal frame that is in excellent conformity with the affected part (see, for example, JP-A-2007-215854).

The workpiece to be subjected to the dental CAD/CAM system is generally called "blank". The blank is required to have machinability as well as properties necessary for a metal frame such as aesthetic appearance, biocompatibility, chemical stability, and abrasion resistance. The machinability is a property for enabling a favorable machining process, and by using a blank having favorable machinability, a metal frame having a desired shape accurately reproduced based on the digitized data generated by the CAD can be efficiently cut out by the CAM.

The alloy disclosed in JP-A-11-1738 is an alloy suited to the casting, but it has a problem in that the machinability is poor. If the machinability of a blank is low, the intended processing cannot be performed so that the shape after processing is deviated from the intended shape. As a result, it takes time and effort to perform a secondary process for correcting the shape and, because the conformity with an affected part is low, patients may feel discomfort.

SUMMARY

An advantage of some aspects of the invention is to provide a dental blank to be machined having excellent machinability, a metal powder for powder metallurgy capable of producing such a dental blank to be machined, a dental metal frame for porcelain bonding having excellent adhesiveness of porcelain, and a dental prosthesis having high reliability.

A dental blank to be machined according to an aspect of the invention contains Co as a main component, Cr in a proportion of 26% by mass or more and 35% by mass or less, Mo in a proportion of 5% by mass or more and 12% by mass or less, and Si in a proportion of 0.5% by mass or more and 1.0% by mass or less, and is formed from a metal powder sintered body.

According to this configuration, a dental blank to be machined having excellent machinability is obtained because it has a structure specific to a sintered body.

In the dental blank to be machined according to the aspect of the invention, it is preferred that a part of the Si is contained as silicon oxide, and the ratio of Si contained as the silicon oxide in the Si is preferably 10% by mass or more and 90% by mass or less.

According to this configuration, effects such as high machinability, high mechanical properties of a metal frame, and high adhesiveness of porcelain are brought about, and also by the existence of a given amount of silicon oxide therein, the amount of oxides of transition metal elements such as Co, Cr, and Mo contained in this blank can be sufficiently reduced. As a result, a dental prosthesis having higher reliability is achieved.

In the dental blank to be machined according to the aspect of the invention, it is preferred that the silicon oxide is segregated at the grain boundary of the sintered body.

According to this configuration, an increase in size of a metal crystal can be more reliably prevented, and thus, a blank from which a metal frame having more excellent mechanical properties can be cut out is obtained. Further, silicon oxide deposits segregated at the grain boundary keep a proper distance from one another by themselves, and therefore, the silicon oxide deposits can be more uniformly dispersed in the blank. As a result, a more homogeneous blank can be obtained.

In the dental blank to be machined according to the aspect of the invention, it is preferred that the existing ratio of $Co_3Mo$ is 0.01% by volume or more and 10% by volume or less.

According to this configuration, an appropriate hardness is imparted to a metal frame, and therefore, a useful blank from the viewpoint of improvement of the reliability of a dental prosthesis is obtained.

In the dental blank to be machined according to the aspect of the invention, it is preferred that in an X-ray diffraction pattern obtained by X-ray diffractometry using a Cu-Kα ray, when the height of the highest peak among the peaks derived from Co identified based on ICDD card is assumed to be 1, the ratio of the height of the highest peak among the peaks derived from $Co_3Mo$ identified based on ICDD card is 0.01 or more and 0.5 or less.

According to this configuration, a blank, which prevents the hardness of a metal frame from decreasing, and is capable of producing a dental prosthesis which strongly resists deformation due to a biting force, and in which a decrease in tensile strength, proof stress, and elongation is prevented, is obtained.

In the dental blank to be machined according to the aspect of the invention, it is preferred that the dental blank to be machined has a 0.2% proof stress of 450 MPa or more, an elongation of 2% or more, and a Young's modulus of 150 GPa or more.

According to this configuration, a blank capable of producing a metal frame having excellent durability is obtained.

In the dental blank to be machined according to the aspect of the invention, it is preferred that the dental blank to be machined has a Vickers hardness of 200 or more and 480 or less.

According to this configuration, a blank capable of producing a metal frame having sufficient deformation resistance also to a biting force is obtained. Further, the machining resistance becomes relatively small so that excellent machinability is obtained, and therefore, a blank from which a metal frame having a desired shape and dimension can be efficiently cut out is obtained.

A metal powder for powder metallurgy according to another aspect of the invention contains Co as a main component, Cr in a proportion of 26% by mass or more and 35% by mass or less, Mo in a proportion of 5% by mass or more and 12% by mass or less, and Si in a proportion of 0.5% by mass or more and 1.0% by mass or less, and is used for producing a dental blank to be machined.

According to this configuration, a metal powder for powder metallurgy capable of producing a dental blank to be machined having excellent machinability is obtained.

A dental metal frame for porcelain bonding according to still another aspect of the invention contains Co as a main component, Cr in a proportion of 26% by mass or more and 35% by mass or less, Mo in a proportion of 5% by mass or more and 12% by mass or less, and Si in a proportion of 0.5% by mass or more and 1.0% by mass or less, and is cut out from a dental blank to be machined which is formed from a metal powder sintered body.

According to this configuration, a dental metal frame for porcelain bonding having excellent adhesiveness of porcelain is obtained.

A dental prosthesis according to yet another aspect of the invention includes the dental metal frame for porcelain bonding according to the aspect of the invention and a porcelain layer provided on the surface of the dental metal frame for porcelain bonding.

According to this configuration, a dental prosthesis, in which the dental metal frame for porcelain bonding and the porcelain layer are strongly adhered to each other so that the reliability is high, is obtained.

In the dental prosthesis according to the aspect of the invention, it is preferred that the porcelain layer contains alumina, and the dental prosthesis further includes a mullite phase disposed between the dental metal frame for porcelain bonding and the porcelain layer.

According to this configuration, a dental prosthesis, in which the porcelain layer and the metal frame are strongly adhered to each other through the mullite phase so that the porcelain layer strongly resists peeling off, and thus the reliability is high, is obtained. Further, it is considered that due to the generation of the mullite phase, the wettability of a ceramic material to the metal frame is improved during a firing treatment. Accordingly, from such a viewpoint, the adhesiveness of the porcelain layer is considered to be enhanced.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

Hereinafter, the dental blank to be machined, the metal powder for powder metallurgy, the dental metal frame for porcelain bonding, and the dental prosthesis according to the invention will be described in detail based on preferred embodiments shown in the accompanying drawings.

Dental Blank to be Machined

First, an embodiment of the dental blank to be machined according to the invention will be described.

Figure 1:
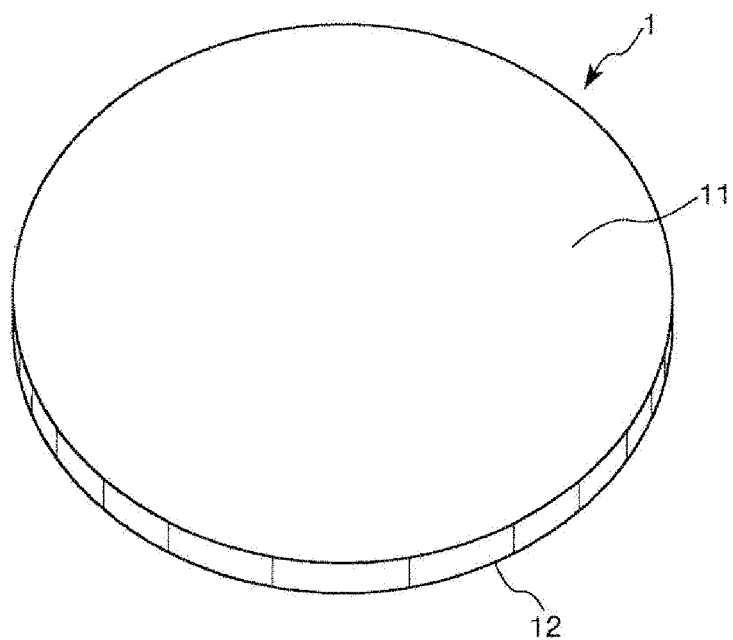
FIG. 1 is a perspective view showing an embodiment of a dental blank to be machined according to the invention.
Figure 2:
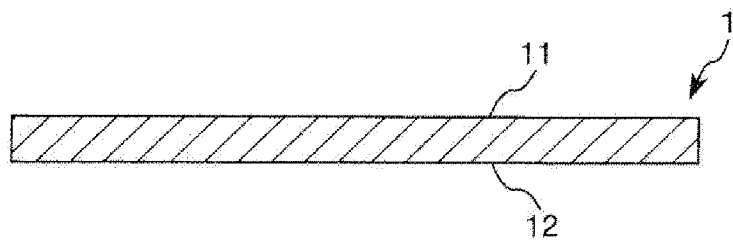
FIG. 2 is a longitudinal cross-sectional view of the dental blank to be machined shown in FIG. 1.

FIG. 1 is a perspective view showing an embodiment of a dental blank to be machined according to the invention, and FIG. 2 is a longitudinal cross-sectional view of the dental blank to be machined shown in FIG. 1.

A dental blank to be machined 1 (hereinafter sometimes abbreviated as "blank 1") shown in FIG. 1 is a member to be used for cutting out a dental metal part having a desired shape by being subjected to a machining process. The dental blank to be machined 1 includes a "mill blank" and a "CAD/CAM blank which are to be machined by a CAM machine of the "dental CAD/CAM system". The dental metal part is not particularly limited as long as it is a metal part which is temporarily or semipermanently retained in the mouth. However, in the following description, a case where a metal frame is cut out will be described.

The blank 1 shown in FIG. 1 has a disk shape, in other words, a cylindrical shape in which the height is smaller than the diameter, and the upper surface 11 and the lower surface 12 thereof are flat (planar) surfaces parallel to each other. The shape of the dental blank to be machined according to the invention is not limited to a disk shape, and may be any shape. For example, the shape may be a rectangular parallelepiped, a cube, a sphere, a polygonal column, or the like.

The diameter of the upper surface 11 and the lower surface 12 of the blank 1 shown in FIG. 1 is not particularly limited, but is set to, for example, about 30 mm or more and 500 mm or less. Further, the thickness of the blank 1 is set appropriately according to the diameter thereof, but is set to, for example, about 3 mm or more and 50 mm or less.

Such a blank 1 is formed from a Co—Cr—Mo—Si-based alloy.

Specifically, the alloy which forms the blank 1 contains Co as a main component, Cr in a proportion of 26% by mass or more and 35% by mass or less, Mo in a proportion of 5% by mass or more and 12% by mass or less, and Si in a proportion of 0.5% by mass or more and 1.0% by mass or less.

The blank 1 formed from such an alloy has not only biocompatibility and chemical stability, but also excellent machinability. Therefore, when a metal frame is cut out by machining the blank 1, machining scraps are smoothly discharged, and also the roughness of the machined surface is sufficiently small, and thus, a stable machining process can be continued over a long period of time. In addition, chipping or abrasion of a machining tool can be minimized. As a result, the amount of machining in the machining process can be made a desired amount, and the metal frame to be cut out can be made to have a dimension and a shape as designed.

Such a metal frame can be attached to an affected part with less sense of discomfort, and thus, a burden on a patient can be minimized and also high adhesiveness and high aesthetic appearance when bonding porcelain thereto can be achieved.

Here, among the constituent elements of this alloy, Co (cobalt) is a main component of the alloy which forms the blank 1, and has a great effect on the basic properties of the blank 1.

The content of Co is set to be the largest of the constituent elements of this alloy, and specifically the content of Co is preferably 50% by mass or more and 67.5% by mass or less, and more preferably 55% by mass or more and 67% by mass or less.

Cr (chromium) mainly acts to improve the corrosion resistance of the blank 1. It is considered that this is because by the addition of Cr, a passivation film (such as $Cr_2O_3$) is easily formed on the alloy, and thus, the chemical stability is improved. By the improvement of the corrosion resistance, an effect that metal ions are hardly eluted even when the alloy comes in contact with, for example, a body fluid is expected. Therefore, it can be said that a metal frame having more excellent biocompatibility can be cut out from the blank 1 formed from an alloy containing Cr. Further, by using Cr along with Co, Mo, and Si, the mechanical properties of the metal frame can be enhanced.

The content of Cr in the alloy which forms the blank 1 is set to 26% by mass or more and 35% by mass or less. If the content of Cr is less than the above lower limit, the corrosion resistance of a metal frame to be cut out from the blank 1 is deteriorated. Therefore, in the case where the metal frame is in contact with a body fluid over a long period of time, metal ions may be eluted. On the other hand, if the content of Cr exceeds the above upper limit, the amount of Cr with respect to Mo or Si is relatively too large, and therefore, the machinability may be deteriorated. In addition, the balance thereof with Co, Mo, or Si is lost to deteriorate the mechanical properties.

The content of Cr is preferably set to 27% by mass or more and 34% by mass or less, and more preferably set to 28% by mass or more and 33% by mass or less.

Mo (molybdenum) mainly acts to enhance the corrosion resistance of the blank 1. That is, by the addition of Mo, the corrosion resistance improved by the addition of Cr can be further enhanced. It is considered that this is because by the addition of Mo, the passivation film containing a Cr oxide as a main material is further densified. Therefore, the Mo-added alloy is more difficult to elute metal ions, and thus contributes to the realization of a metal frame having particularly high biocompatibility.

The content of Mo in the alloy which forms the blank 1 is set to 5% by mass or more and 12% by mass or less. If the content of Mo is less than the above lower limit, the corrosion resistance of a metal frame to be cut out from the blank 1 may be insufficient. On the other hand, if the content of Mo exceeds the above upper limit, the amount of Mo with respect to Cr or Si is relatively too large, and therefore, the machinability may be deteriorated.

The content of Mo is preferably set to 5.5% by mass or more and 11% by mass or less, and more preferably set to 6% by mass or more and 9% by mass or less.

Si (silicon) mainly acts to enhance the machinability of the blank 1. By the addition of Si, silicon oxide is formed by oxidizing a part of Si in the blank 1. Examples of the silicon oxide include SiO and $SiO_2$. When such silicon oxide is formed in the blank 1, a metal crystal is divided at the site. Therefore, it is presumed that the structure of the blank 1 is locally discontinuous around the silicon oxide. It is considered that when the blank 1 in such a state is machined using a machining tool, machining scraps generated by the tip end of the machining tool easily fall off from the main body of the blank 1 with the silicon oxide used as the starting point. As a result, it is considered that the machining resistance is decreased and thus the machinability of the blank 1 is enhanced.

On the other hand, Si also acts to enhance the mechanical properties of a metal frame to be cut out from the blank 1. The above-described silicon oxide prevents a significant increase in size of a metal crystal when the metal crystal grows in the production of the blank 1. Due to this, in the Si-added alloy, the particle diameter of the metal crystal is suppressed to be small, and thus, the mechanical properties of the metal frame can be further enhanced.

Accordingly, by the addition of Si, both the machinability of the blank 1 and the mechanical properties of a metal frame to be cut out from the blank 1 can be achieved.

Moreover, by the addition of Si, the adhesiveness of porcelain to a metal frame to be cut out from the blank 1 is improved. Therefore, when a porcelain layer is provided so as to cover the surface of the metal frame, the peeling off of the porcelain layer is prevented, and thus, a dental prosthesis having high reliability is obtained.

In order to obtain the effect as described above, it is desired to set the content of Si to 0.5% by mass or more and 1.0% by mass or less. If the content of Si is less than the above lower limit, the amount of silicon oxide is also decreased, and therefore, the machining resistance is increased to deteriorate the machinability of the blank 1, and also the size of a metal crystal is liable to increase in the production of the blank 1, and therefore, a possibility that the mechanical properties of a metal frame to be cut out from the blank 1 are also deteriorated is increased. Further, the adhesiveness of porcelain to the metal frame also becomes insufficient, and therefore, a problem such as peeling off of the porcelain layer in a dental prosthesis is liable to occur. On the other hand, if the content of Si exceeds the above upper limit, the amount of silicon oxide present in the blank 1 is too large, and a region where silicon oxide is spatially distributed in a continuous manner is liable to be formed. In such a region, the structure of the blank 1 is discontinuous at a given size, and therefore, when an external force is applied to the blank 1, this region is liable to serve as the starting point of destruction. As a result, the mechanical properties of the blank 1 are deteriorated.

The content of Si is preferably set to 0.55% by mass or more and 0.95% by mass or less, and more preferably set to 0.6% by mass or more and 0.9% by mass or less.

Further, a part of the Si preferably exists in the form of silicon oxide as described above, however, as for the existing amount thereof, the ratio of Si contained as silicon oxide with respect to the total amount of Si is preferably 10% by mass or more and 90% by mass or less, more preferably 20% by mass or more and 80% by mass or less, further more preferably 30% by mass or more and 70% by mass or less, and particularly preferably 35% by mass or more and 65% by mass or less. By setting the ratio of Si contained as silicon oxide with respect to the total amount of Si within the above range, the effects such as machinability, mechanical properties of the metal frame, and adhesiveness of porcelain as described above are brought about, and also by the existence of a given amount of silicon oxide therein, the amount of oxides of transition metal elements such as Co, Cr, and Mo contained in this blank 1 can be sufficiently reduced. It is considered that this is namely because Si is more easily oxidized than Co, Cr, and Mo, and deprives oxygen bonded to these transition metal elements to cause a reduction reaction, and therefore, the fact that not the total amount of Si is silicon oxide means that a sufficient reduction reaction is caused with respect to the transition metal elements. Accordingly, by setting the ratio of Si contained as silicon oxide to the total amount of Si within the above range, in the blank 1, the effect such as high machinability, high mechanical properties of the metal frame, and high adhesiveness of porcelain as described above are prevented from being inhibited by an oxide of Co, Cr, or Mo. As a result, a dental prosthesis having higher reliability is realized.

Further, by setting the ratio of Si contained as silicon oxide in the Si within the above range, an appropriate hardness is imparted to the blank 1. That is, it is considered that by the existence of a given amount of Si which is not in the form of silicon oxide, Si and at least one element selected from Co, Cr, and Mo produce a hard intermetallic compound, which increases the hardness of the blank 1. When the hardness of the blank 1 is increased, the hardness of a metal frame to be cut out from the blank 1 is also increased, and therefore, a dental prosthesis including this metal frame strongly resists deformation due to a biting force after it is attached to an affected part, and thus the reliability is enhanced. In other words, by the addition of Si, significant growth of a metal crystal is inhibited, and therefore, the hardness of the blank 1 tends to be decreased from this viewpoint, however, a part of Si forms an intermetallic compound, and therefore, a significant decrease in the hardness is prevented, and the reliability as a dental prosthesis can be ensured.

This intermetallic compound is not particularly limited, however, examples thereof include $CoSi_2$, $Cr_3Si$, $MoSi_2$, and $Mo_5Si_3$.

The ratio of Si contained as silicon oxide to the total amount of Si can be determined using gravimetry and ICP optical emission spectroscopy.

Further, in consideration of the amount of the intermetallic compound deposited, the ratio of the Si content to the Mo content (Si/Mo) is preferably 0.05 or more and 0.2 or less, and more preferably 0.08 or more and 0.15 or less in terms of mass ratio. According to this, a blank 1 capable of producing a dental prosthesis having high reliability is obtained while preventing a significant decrease in the machinability of the blank 1.

The silicon oxide may be distributed at any place, but is preferably distributed in a segregated manner at the grain boundary (the boundary surface between metal crystals). By segregating the silicon oxide at such a place, an increase in size of a metal crystal can be more reliably prevented, and thus, a blank 1 from which a metal frame having more excellent mechanical properties can be cut out is obtained. Further, silicon oxide deposits segregated at the grain boundary keep a proper distance from one another by themselves, and therefore, the silicon oxide deposits can be more uniformly dispersed in the blank 1. As a result, a more homogeneous blank 1 can be obtained.

Such a blank 1 contributes to the minimization of individual differences in the characteristics of metal frames even in the case where a plurality of metal frames are cut out from the blank 1.

Further, the segregated silicon oxide deposits can be analyzed to specify the size, distribution, and the like thereof by an area analysis of a qualitative analysis. Specifically, in a compositional image of Si obtained by an electron beam microanalyzer (EPMA), an average diameter of a region where Si is segregated is preferably 0.1 μm or more and 10 μm or less, and more preferably 0.3 μm or more and 8 μm or less. When the average diameter of a region where Si is segregated is within the above range, the size of the silicon oxide deposit becomes most suitable for exhibiting the respective effects as described above. That is, if the average diameter of a region where Si is segregated is less than the above lower limit, the silicon oxide deposits are not segregated in a region having a sufficient size, and the above-described respective effects may not be sufficiently obtained. On the other hand, if the average diameter of a region where Si is segregated exceeds the above upper limit, the mechanical properties of the blank 1 may be deteriorated.

The average diameter of a region where Si is segregated can be determined as an average of the diameter of a circle having the same area (projected area circle equivalent diameter) as that of the region where Si is segregated in the compositional image of Si. Further, the average diameter of a region where Si is segregated is determined as an average of measurement values of 100 or more regions where Si is segregated.

Further, the blank 1 includes a first phase formed mainly from Co and a second phase formed mainly from $Co_3Mo$. By including the second phase of these phases, an appropriate hardness is imparted to a metal frame in the same manner as the intermetallic compound containing Si described above, and therefore, a useful blank 1 from the viewpoint of improvement of the reliability of a dental prosthesis is obtained. On the other hand, in the case where the second phase is included excessively, the second phase is liable to be segregated, and thus, the mechanical properties such as tensile strength, proof stress, and elongation are deteriorated.

Therefore, it is preferred that the first phase and the second phase are included at an appropriate ratio from the above viewpoint. Specifically, for the blank 1, a crystal structure analysis is performed by X-ray diffractometry using a Cu-Kα ray, and when the height of the highest peak among the peaks derived from Co is assumed to be 1, the height of the highest peak among the peaks derived from $Co_3Mo$ is preferably 0.01 or more and 0.5 or less, and more preferably 0.02 or more and 0.4 or less.

If the ratio of the height of the highest peak of $Co_3Mo$ when the height of the highest peak of Co is assumed to be 1 is less than the above lower limit, the ratio of $Co_3Mo$ to Co in the blank 1 is decreased, and therefore, the hardness of the metal frame is decreased so that a dental prosthesis which is easily deformed by a biting force may be formed. On the other hand, if the ratio of the height of the highest peak of $Co_3Mo$ exceeds the above upper limit, the amount of $Co_3Mo$ existing is too large, and therefore, $Co_3Mo$ is liable to be segregated so that the tensile strength and the proof stress are decreased, and also the elongation may be decreased.

The Cu-Kα ray is generally a characteristic X-ray with an energy of 8.048 keV.

Further, when a peak derived from Co is identified, the identification is performed based on the database of Co of ICDD (The International Centre for Diffraction Data) card. Similarly, when a peak derived from $Co_3Mo$ is identified, the identification is performed based on the database of $Co_3Mo$ of ICDD card.

The existing ratio of the second phase in the blank 1 is preferably 0.01% by volume or more and 10% by volume or less, and more preferably 0.05% by volume or more and 5% by volume or less. According to this, a metal frame having appropriate hardness, tensile strength, proof stress, and elongation is obtained, and a dental prosthesis which strongly resists deformation due to a biting force is obtained.

The alloy which forms the blank 1 may also contain C (carbon) other than the elements as described above. By the addition of C, the hardness and the tensile strength of the blank 1 are further increased, and also the machinability is further enhanced. A detailed reason for further enhancing the machinability is not clear, however, a decrease in machining resistance by the formation of a carbide is considered to be one reason therefor.

The content of C in the alloy which forms the blank 1 is not particularly limited, but is preferably 1.5% by mass or less, and more preferably 0.7% by mass or less. If the content of C exceeds the above upper limit, the brittleness of the blank 1 is increased so that the mechanical properties may be deteriorated.

The lower limit of the additional amount of C is not particularly set, however, in order to sufficiently exhibit the above-described effect, the lower limit thereof is preferably set to about 0.05% by mass.

Further, the content of C is preferably about 0.02 times or more and 0.5 times or less, and more preferably about 0.05 times or more and 0.3 times or less the content of Si. It is considered that by setting the ratio of C to Si within the above range, silicon oxide and a carbide synergistically act to improve the machinability while minimizing the adverse effect thereof on the mechanical properties of the blank 1. Accordingly, a blank 1 having particularly excellent machinability can be obtained.

In addition, the alloy which forms the blank 1 may include, other than the elements as described above, a small amount of an additive to be added deliberately within a range in which the above-described effect is not impaired and an impurity inevitably generated during the production. In this case, the total content of the additive and the impurity is preferably set to 1% by mass or less, more preferably 0.5% by mass or less, and further more preferably 0.2% by mass or less. Examples of such an additive element and an impurity element include Li, Be, B, N, O, Na, Mg, Al, P, S, Mn, K, Ca, Sc, Ti, V, Co, Zn, Ga, Ge, Y, Pd, Ag, In, Sn, Sb, Hf, Ta, W, Os, Ir, Pt, Au, and Bi.

On the other hand, it is preferred that the alloy which forms the blank 1 does not substantially contain Ni (nickel). Ni is often contained in a given amount in a blank in the related art for ensuring plastic workability. However, Ni is sometimes treated as a causative substance of metal allergy and is an element suspected to have an adverse effect on a living body. To the alloy which forms the blank 1, Ni as a constituent element is not added except for Ni inevitably mixed therein during the production. As a result, a metal frame to be cut out from the blank 1 according to the invention is likely not to cause a metal allergy, and thus has particularly high biocompatibility. Incidentally, in the invention, by the addition of an appropriate amount of Si, a blank 1 having sufficient machinability is realized even if Ni is not added. Further, in consideration of a case where Ni is inevitably mixed therein, the content of Ni is preferably 0.05% by mass or less, and more preferably 0.03% by mass or less.

The remainder of the alloy which forms the blank 1 other than the elements as described above is Co. As described above, the content of Co is set to be the largest of the elements contained in the alloy which forms the blank 1.

The respective constituent elements of the alloy which forms the blank 1 and the compositional ratio thereof can be determined by, for example, atomic absorption spectrometry specified in JIS G 1257(2000), ICP optical emission spectroscopy specified in JIS G 1258 (2007), spark optical emission spectroscopy specified in JIS G 1253 (2002), X-ray fluorescence spectroscopy specified in JIS G 1256 (1997), gravimetry, titrimetry, and absorption spectroscopy specified in JIS G 1211 (2011), JIS G 1212(1997), JIS G 1213 (2001), JIS G 1214(1998), JIS G 1215(2010), JIS G 1216(1997), JIS G 1217(2005), JIS G 1218(1999), JIS G 1219(1997), JIS G 1220(1994), JIS G 1221(1998), JIS G 1222(1999), JIS G 1223(1997), JIS G 1224(2001), JIS G 1225(2006), JIS G 1226(1994), JIS G 1227(1999), JIS G 1228(2006), JIS G 1229(1994), JIS G 1232(1980), JIS G 1233(1994), JIS G 1234(1981), JIS G 1235(1981), JIS G 1236(1992), JIS G 1237(1997), or the like. Specifically, a solid optical emission spectrometer (spark optical emission spectrometer) (model: SPECTROLAB, type: LAVMB08A) manufactured by SPECTRO Analytical Instruments GmbH can be used.

Further, when C (carbon) and S (sulfur) are determined, particularly, an infrared absorption method after combustion in a current of oxygen (after combustion in a high-frequency induction furnace) specified in JIS G 1211(2011) is also used. Specifically, a carbon-sulfur analyzer, CS-200 manufactured by LECO Corporation can be used.

Further, when N (nitrogen) and O (oxygen) are determined, particularly, a method for determination of nitrogen content in iron and steel specified in JIS G 1228 (2006) and a method for determination of oxygen content in metallic materials specified in JIS Z 2613(2006) are also used. Specifically, an oxygen-nitrogen analyzer, TC-300/EF-300 manufactured by LECO Corporation can be used.

The blank 1 shown in FIG. 1 is formed from a metal powder sintered body, that is, it is produced by powder metallurgy. Such a blank 1 has more excellent mechanical properties such as hardness, tensile strength, proof stress, and elongation as compared with those (ingot materials) produced by, for example, casting. It is considered that this is because the blank 1 produced by powder metallurgy is formed from a metal powder obtained by quenching (since the volume is small, it is easily quenched), and therefore, significant grain growth of a metal crystal is more difficult to occur than in the case of using a casting method or the like, and as a result, it is difficult to form a metal crystal with an increased size. According to the powder metallurgy, a homogeneous composition is easily obtained, and therefore, uniform distribution of Si and silicon oxide is also easily obtained. Accordingly, a blank 1 in which the machinability is uniform is obtained.

Further, the blank 1 formed from a metal powder sintered body has a characteristic that the content of a dendrite phase is very low. Specifically, the blank 1 is observed with a scanning electron microscope, and in the obtained observation image, the area ratio of the dendrite phase is preferably 20% or less, and more preferably 10% or less. The blank 1 satisfying such conditions has particularly excellent mechanical properties and machinability.

This area ratio is calculated as a ratio of the area of the dendrite phase to the area of the observation image, and the length of one side of the observation image is set to about 50 μm or more and 1000 μm or less.

As the metal powder to be used for the production of the blank 1 (metal powder for powder metallurgy according to the invention), a powder formed from the alloy as described above is used. The average particle diameter thereof is preferably 3 μm or more and 100 μm or less, more preferably 4 μm or more and 80 μm or less, and further more preferably 5 μm or more and 60 μm or less. By using a metal powder having such a particle diameter, a blank 1 having excellent mechanical properties and machinability can be obtained.

The average particle diameter is obtained as a particle diameter when the cumulative amount on a mass basis is 50% in the particle size distribution obtained by laser diffractometry.

If the average particle diameter of the metal powder is less than the above lower limit, the moldability in powder metallurgy is deteriorated, and therefore, the density of the blank 1 is decreased so that the mechanical properties of the metal frame may be deteriorated. On the other hand, if the average particle diameter of the metal powder exceeds the above upper limit, the packing density of the metal powder in powder metallurgy is decreased, and therefore, also in this case, the density of the blank 1 is decreased so that the mechanical properties of the metal frame may be deteriorated. Further, the uniformity of the composition is deteriorated so that the machinability of the blank 1 may be deteriorated.

The particle size distribution of the metal powder is preferably as narrow as possible. Specifically, when the average particle diameter of the metal powder is within the above range, the maximum particle diameter of the metal powder is preferably 200 μm or less, and more preferably 150 μm or less. By controlling the maximum particle diameter of the metal powder within the above range, the particle size distribution of the metal powder can be made narrower, and the mechanical properties and machinability of the blank 1 can be further improved.

Here, the "maximum particle diameter" refers to a particle diameter when the cumulative amount on a mass basis is 99.9% in the particle size distribution obtained by laser diffractometry.

The average of the aspect ratio of the particle of the metal powder defined by PS/PL wherein PS (μm) represents the minor axis of each particle and PL (μm) represents the major axis thereof is preferably about 0.4 or more and 1 or less, and more preferably about 0.7 or more and 1 or less. The metal powder having an aspect ratio within this range has a shape relatively close to a spherical shape, and therefore, the packing factor when the powder is compact-molded is increased. As a result, a blank 1 having high mechanical properties and machinability can be obtained.

Here, the "major axis" is the maximum length in the projected image of the particle, and the "minor axis" is the maximum length in the direction perpendicular to the major axis. Incidentally, the average of the aspect ratio is obtained as an average of measurement values of 100 or more particles of the metal powder.

On the other hand, the average of the aspect ratio in the cross section of the blank 1 defined by CS/CL wherein CL represents the major axis of each crystal structure and CS represents the minor axis thereof is preferably about 0.4 or more and 1 or less, and more preferably about 0.5 or more and 1 or less. The crystal structure having such an aspect ratio has small anisotropy, and therefore contributes to the realization of a blank 1 capable of producing a metal frame having excellent mechanical properties such as proof stress regardless of the direction of a force applied. That is, a metal frame cut out from such a blank 1 has excellent fracture resistance even when it is used in any posture. Therefore, the place of use in the mouth is not limited, and therefore, such a blank 1 is useful. In other words, according to such a blank 1, a metal frame having excellent mechanical properties can be produced regardless of the way of cutting out the metal frame.

Here, the "major axis" is the maximum length in one crystal structure in the observation image of the cross section of the blank 1, and the "minor axis" is the maximum length in the direction perpendicular to the major axis. Incidentally, the average of the aspect ratio is obtained as an average of measurement values of 100 or more crystal structures.

It is preferred that the blank 1 has independent small pores therein. As having such pores, the blank 1 has particularly excellent machinability. It is considered that this is because by the existence of the independent pores, deterioration of the mechanical properties of the blank 1 is prevented, and also machining scraps generated during the machining process particularly easily fall off from the main body of the blank 1 with the pores used as the starting points, and therefore, an action to greatly decrease the machining resistance is obtained.

Further, as the blank 1 has pores, a metal frame to be cut out from the blank 1 also has pores opening to the surface. Such pores enable the constituent material of porcelain to enter the pores when bonding porcelain to the metal frame by firing. Therefore, the pores contribute to the enhancement of the adhesiveness between the metal frame and the porcelain. As a result, when a porcelain layer is provided so as to cover the surface of the metal frame, the peeling off of the porcelain layer is prevented, and thus, a dental prosthesis having high reliability can be obtained.

The average diameter of the pores is preferably 0.1 μm or more and 10 μm or less, and more preferably 0.3 μm or more and 8 μm or less. When the average diameter of the pores is within the above range, a blank 1 having higher machinability is obtained. That is, if the average diameter of the pores is less than the above lower limit, the machinability may not be sufficiently enhanced, and on the other hand, if the average diameter of the pores exceeds the above upper limit, the mechanical properties of the blank 1 may be deteriorated.

The average diameter of the pores can be obtained as an average of the diameter of a circle having the same area as that of a pore (projected area circle equivalent diameter) in a scanning electron microscope image. Further, the average diameter of the pores is obtained as an average of measurement values of 100 or more pores.

The area ratio of the pores in the observation image of the blank 1 is preferably 0.001% or more and 1% or less, and more preferably 0.005% or more and 0.5% or less. When the area ratio of the pores is within the above range, both the mechanical properties and the machinability of the blank 1 can be more highly achieved.

This area ratio is calculated as a ratio of the area of the pores to the area of the observation image, and the length of one side of the observation image is set to about 50 μm or more and 1000 μm or less.

The Vickers hardness of the blank 1 is preferably 200 or more and 480 or less, and more preferably 240 or more and 380 or less. Further, the blank 1 having such a hardness is capable of producing a metal frame having sufficient deformation resistance to a biting force. Further, the blank 1 having such a hardness has relatively small machining resistance, and therefore has excellent machinability, and thus, a metal frame having a desired shape and dimension can be efficiently cut out from the blank 1.

The Vickers hardness of the blank 1 is measured in accordance with the test method specified in JIS Z 2244 (2009).

The tensile strength of the blank 1 is preferably 520 MPa or more, and more preferably 600 MPa or more and 1500 MPa or less. The blank 1 having such a tensile strength is capable of producing a metal frame having excellent durability.

Similarly, the 0.2% proof stress of the blank 1 is preferably 450 MPa or more, and more preferably 500 MPa or more and 1200 MPa or less. The blank 1 having such a 0.2% proof stress is capable of producing a metal frame having excellent durability just the same.

The tensile strength and the 0.2% proof stress are measured in accordance with the test method specified in JIS Z 2241(2011).

Further, the elongation of the blank 1 is preferably 2% or more and 50% or less, and more preferably 10% or more and 45% or less. The blank 1 having such an elongation rarely experiences a chip, a crack, or the like, and thus, the blank 1 has excellent machinability.

The elongation (elongation at break) of the blank 1 is measured in accordance with the test method specified in JIS Z 2241(2011).

The Young's modulus of the blank 1 is preferably 150 GPa or more, and more preferably 170 GPa or more and 300 GPa or less. The blank 1 having such a Young's modulus strongly resists deformation, and therefore enables a machining process with high dimensional accuracy and also can realize a metal frame which strongly resists deformation due to a biting force.

The fatigue strength of the blank 1 is preferably 250 MPa or more, more preferably 350 MPa or more, and further more preferably 500 MPa or more and 1000 MPa or less. The blank 1 having such a fatigue strength can realize a metal frame which prevents the occurrence of a fatigue crack or the like even if it is used in an environment in which a load is repeatedly applied thereto in a state of, for example, being in contact with a body fluid in the mouth, and can exhibit its function over a long period of time.

The fatigue strength of the blank 1 is measured in accordance with the test method specified in JIS T 0309(2009). The waveform of an applied load corresponding to repeated stress is set to a sine wave, and the stress ratio (minimum stress/maximum stress) is set to 0.1. Further, the repeated frequency is set to 30 Hz, and the repeat count is set to $1 \times 10^7$.

Such a blank 1 has a small machining resistance as described above, and therefore has excellent machinability. That is, the machining resistance of the blank 1 is smaller than that of an ingot material having the same composition as that of a metal powder to be used for the production of the blank 1. A small machining resistance leads to suppression of the amplitude of vibration of a processing tool during machining to be small. Therefore, when the blank 1 is machined, a desired shape can be easily and accurately cut out, and thus, a metal frame having high dimensional accuracy can be produced.

Specifically, the machining resistance of the blank 1 is preferably 300 N or less, more preferably 250 N or less, and further more preferably 200 N or less. The blank 1 which can be processed at such a relatively small machining resistance has high machinability, and thus can be processed with high processing accuracy.

The machining resistance of the blank 1 can be measured by using, for example, a three-component tool dynamometer.

Figure 3:
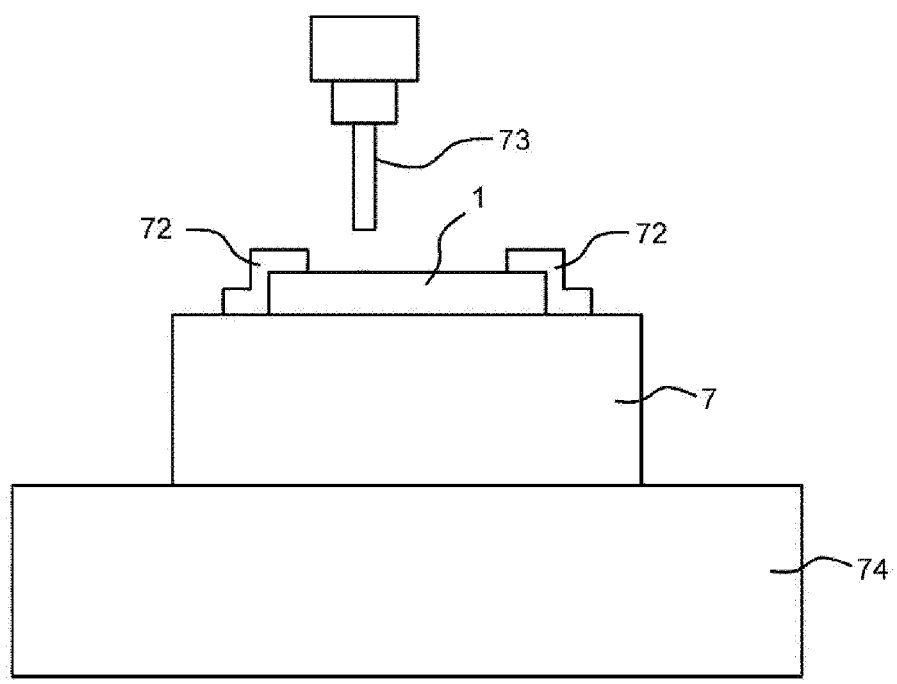
FIG. 3 is a view for explaining a method for measuring the machining resistance of the dental blank to be machined according to the invention.

FIG. 3 is a view for explaining a method for measuring the machining resistance of the blank 1.

When the machining resistance of the blank 1 is measured, first, as shown in FIG. 3, a three-component tool dynamometer 7 is placed on a stage 74 of a processing device. Subsequently, the blank 1 is fixed on a measurement section 71 of the three-component tool dynamometer 7. In the fixation, a fixture 72 with a screw is used, and a screw fastening torque is set to 30 kN. In such a state, the blank 1 is machined using a processing tool 73. Then, among the machining resistances of the components in the three directions (x, y, and z components) measured by the three-component tool dynamometer 7 during processing, the maximum value can be adopted as the machining resistance of the blank 1. Further, the machining resistance in a wet process is a machining resistance when performing processing using a machining fluid.

Figure 4A:
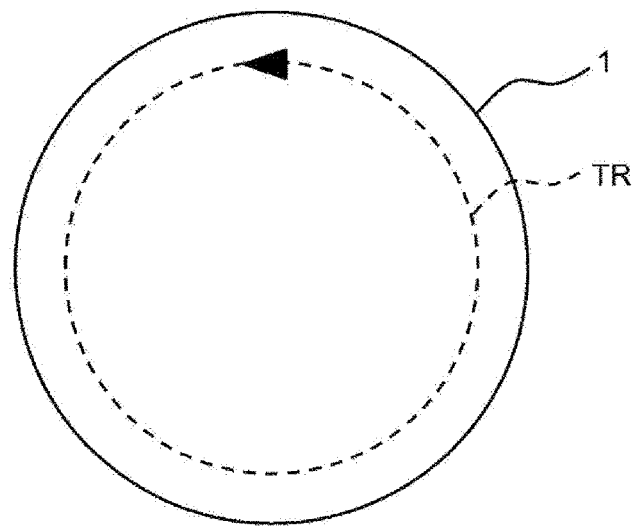
FIGS. 4A and 4B are views each showing a scanning track of a processing tool for a blank when the machining resistance of the dental blank to be machined according to the invention is measured.
Figure 4B:
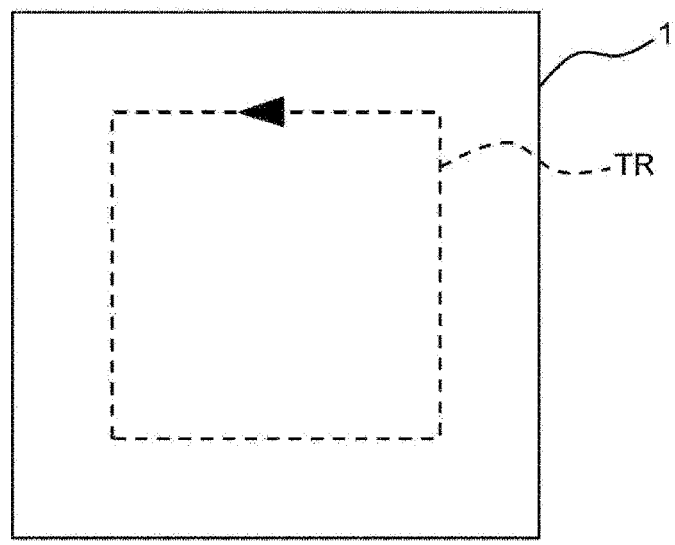

FIGS. 4A and 4B are views each showing a scanning track TR of the processing tool 73 for the blank 1 when the machining resistance of the blank 1 is measured. When the machining resistance of the blank 1 is measured, the processing tool 73 may be allowed to scan the track TR along the contour of the blank 1. For example, in the case where the contour of the blank 1 is a circle, as shown in FIG. 3A, the processing tool 73 may be allowed to scan the track TR in a circular path, and in the case where the contour of the blank 1 is a rectangle, as shown in FIG. 3B, the processing tool 73 may be allowed to scan the track TR in a rectangular path.

Further, the blank 1 is highly homogeneous, and therefore has a characteristic that a difference in machining resistance between a surface layer portion and an inner layer portion of the blank 1 is small. Therefore, the machining resistance is prevented from changing during the machining process of the blank 1, and the dimensional accuracy of a metal frame to be cut out can be prevented from deteriorating.

Specifically, for example, when the blank 1 has a plate shape having a thickness of 10 mm or more, in the cross section along the thickness direction of the blank 1, a portion at a depth of 0.3 mm from the surface is determined as the surface layer portion, and a portion at a depth of 5 mm from the surface is determined as the inner layer portion.

At this time, the machining resistance in the inner layer portion is preferably 50% or more and 200% or less, more preferably 60% or more and 175% or less, and further more preferably 75% or more and 150% or less of the machining resistance in the surface layer portion. According to this, a decrease in the processing accuracy of the blank 1 caused by a variation in the machining resistance can be prevented. Incidentally, in the case where the machining resistance in the inner layer portion is less than the above lower limit, a difference in machining resistance between the inner layer portion and the surface layer portion is increased, and therefore, the processing accuracy may be deteriorated depending on the positional relationship between the blank 1 and the processing tool. That is, the machining resistance in the inner layer portion is very smaller than the machining resistance in the surface layer portion, and therefore, for example, when the processing tool which is processing the surface layer portion gradually moves toward the inner layer portion, the machining resistance decreases to lose the relationship between a driving force and a machining result, and thus, unintended processing may occur. On the other hand, also in the case where the machining resistance in the inner layer portion exceeds the above upper limit, the processing accuracy may be deteriorated depending on the positional relationship between the blank 1 and the processing tool just the same. That is, the machining resistance in the inner layer portion is very larger than the machining resistance in the surface layer portion, and therefore, for example, when the processing tool which is processing the surface layer portion gradually moves toward the inner layer portion, the machining resistance increases to lose the relationship between a driving force and a machining result, and thus, unintended processing may occur.

The blank 1 is useful in that the machining resistance is relatively suppressed to be low not only in a wet machining process, but also in a dry machining process. That is, the blank 1 has a characteristic that a difference in machining resistance between a wet machining process and a dry machining process is small. Therefore, depending on the shape of a metal frame to be cut out from the blank 1, a metal frame having high dimensional accuracy can be cut out even by a dry machining process.

Specifically, when the machining resistance in a wet machining process is assumed to be 1, the machining resistance in a dry machining process is preferably 2 or less, and more preferably 1.5 or less. When the machining resistance in a dry machining process with respect to the machining resistance in a wet machining process is within the above range, a metal frame having sufficiently high dimensional accuracy can be cut out from the blank 1 even by a dry machining process, and therefore, such a blank 1 is useful in that the machining process can be easily performed.

It is not necessary to use a machining fluid in a dry machining process, and therefore, the dry machining process has an advantage that time and effort for washing a metal frame cut out from the blank 1 can be saved. In particular, in the case of a material retained in the body such as a metal frame, it is desired to prevent the machining fluid from remaining as much as possible, and therefore, it is effective to be able to adopt a dry machining process also from the viewpoint of safety of a metal frame to be cut out, or the like.

In the wet machining process of the blank 1, also in the case where an aqueous machining fluid is used instead of an oil-based machining fluid, a favorable machining result is obtained. The aqueous machining fluid can be relatively easily removed, and therefore, time and effort for washing can be reduced. In addition, the blank 1 can bring about a favorable machining result also by a semi-dry process (MQL process) in which processing is performed using a small amount of a machining fluid, and therefore, it is possible to cut out a metal frame having high dimensional accuracy while significantly reducing the amount of machining fluid used.

Examples of the metal powder to be used for the production of the blank 1 include those produced by a variety of powdering methods such as an atomization method (such as a water atomization method, a gas atomization method, or a spinning water atomization method), a reducing method, a carbonyl method, and a pulverization method.

Among these, a metal powder produced by an atomization method is preferably used, and a metal powder produced by a water atomization method or a spinning water atomization method is more preferably used. The atomization method is a method in which a molten metal (a metal melt) is caused to collide with a fluid (a liquid or a gas) sprayed at a high speed to atomize the metal melt, followed by cooling, whereby a metal powder is produced. By producing the metal powder through such an atomization method, an extremely fine powder can be efficiently produced. Further, the shape of the particle of the obtained powder is closer to a spherical shape by the action of surface tension. Due to this, a molded body having a high packing factor is obtained when such a metal powder is molded by powder metallurgy. Accordingly, a blank 1 having excellent mechanical properties is obtained.

In the case where a water atomization method is used as the atomization method, the pressure of water (hereinafter referred to as "atomization water") to be sprayed to the molten metal is not particularly limited, but is preferably set to about 75 MPa or more and 120 MPa or less (750 kgf/cm$^2$ or more and 1200 kgf/cm$^2$ or less), and more preferably about 90 MPa or more and 120 MPa or less (900 kgf/cm$^2$ or more and 1200 kgf/cm$^2$ or less).

The temperature of the atomization water is also not particularly limited, but is preferably set to about 1° C. or higher and 20° C. or lower.

The atomization water is often sprayed in a cone shape such that it has a vertex on the fall path of the metal melt and the outer diameter gradually decreases downward. In this case, the vertex angle θ of the cone formed by the atomization water is preferably about 10° or more and 40° or less, and more preferably about 15° or more and 35° or less. According to this, a metal powder having a composition as described above can be reliably produced.

Further, by using a water atomization method (particularly, a spinning water atomization method), the metal melt can be particularly quickly cooled. Due to this, a blank 1 which has excellent mechanical properties and machinability, and also is homogeneous, is obtained.

The cooling rate when cooling the metal melt in the atomization method is preferably $1 \times 10^{4}$° C./s or more, and more preferably $1 \times 10^{5}$° C./s or more. By the quick cooling in this manner, a metal powder in which the grain diameter of a metal crystal is particularly small is obtained.

Further, in the case where a molten metal is obtained by melting the starting material, when the melting point of the constituent material of the blank 1 is represented by Tm, the melting temperature of the starting material is preferably set to about Tm+50° C. or higher and Tm+300° C. or lower, and more preferably set to about Tm+100° C. or higher and Tm+200° C. or lower. According to this, when a molten metal is finely atomized by colliding with a fluid, it becomes easy to control the production of an alloy to be constant. That is, an alloy having a high purity (low oxygen content) is easily produced while preventing an increase in size of the crystal structure. Further, for example, the degree of oxidation of silicon is easily controlled. Due to this, a metal powder particularly suitable for the production of the blank 1 can be produced.

The thus obtained metal powder is molded by any of a variety of molding methods, whereby a molded body is obtained. Examples of the molding method include a press-molding method, an extrusion-molding method, and an injection-molding method.

Thereafter, the obtained molded body is degreased and fired, whereby a sintered body (blank 1) is obtained. The firing temperature is appropriately set according to the composition of the alloy, but is set to, for example, about 900° C. or higher and 1400° C. or lower.

For the thus obtained sintered body, an HIP treatment (hot isostatic pressing treatment) or the like may also be performed. By doing this, the density of the sintered body is further increased, and thus, a blank 1 having more excellent mechanical properties can be obtained.

The conditions for the HIP treatment are set, for example, as follows: the temperature is 850° C. or higher and 1200° C. or lower, and the time is about 1 hour or more and 10 hours or less.

Further, the pressure to be applied is preferably 50 MPa or more, and more preferably 100 MPa or more.

Dental Metal Frame for Porcelain Bonding

Next, an embodiment of the dental metal frame for porcelain bonding according to the invention will be described.

Figure 5:
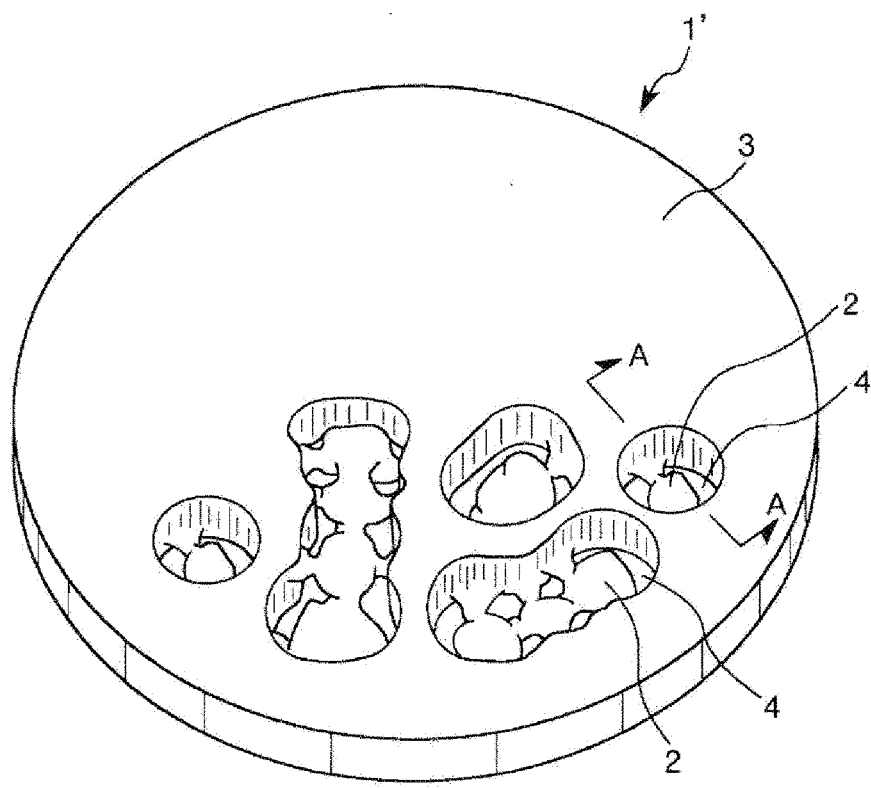
FIG. 5 is a perspective view showing a state of a blank after an embodiment of a dental metal frame for porcelain bonding according to the invention is cut out from the blank shown in FIG. 1.
Figure 6:
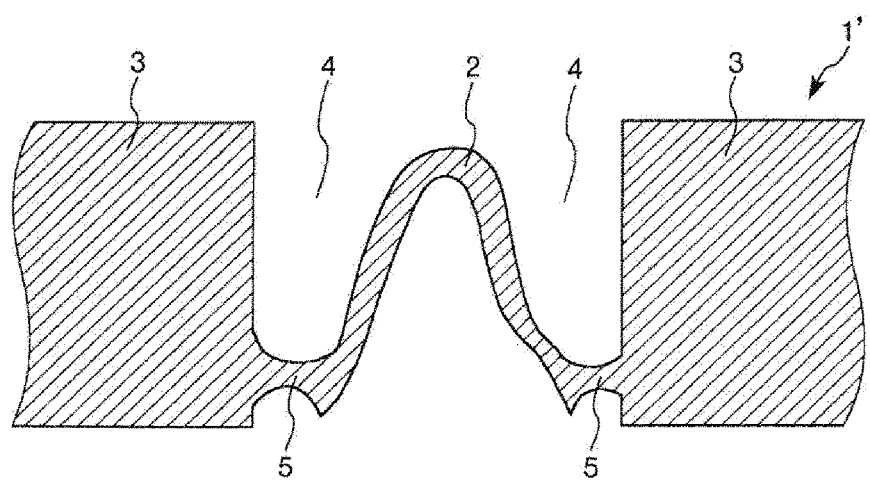
FIG. 6 is a cross-sectional view taken along the line A-A in FIG. 5.
Figure 7:
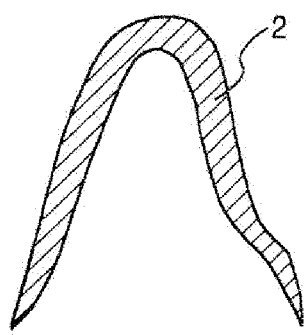
FIG. 7 is a longitudinal cross-sectional view showing the embodiment of the dental metal frame for porcelain bonding according to the invention.

FIG. 5 is a perspective view showing a state of a blank after an embodiment of a dental metal frame for porcelain bonding according to the invention is cut out from the blank shown in FIG. 1, FIG. 6 is a cross-sectional view taken along the line A-A in FIG. 5, and FIG. 7 is a longitudinal cross-sectional view showing the embodiment of the dental metal frame for porcelain bonding according to the invention.

A blank 1' after the machining process shown in FIG. 5 is in a state after a metal frame 2 is cut out by machining the blank 1. The metal frame 2 is a member to be used as a base material of a dental prosthesis such as an inlay, a crown, a bridge, a denture, a metal denture base, an implant, an abutment, a fixture, or a screw. Therefore, the shape of the dental prosthesis is roughly determined by the metal frame 2, and therefore, the shape of the metal frame 2 to be cut out generally corresponds to the shape of the dental prosthesis to be produced. Then, by providing a porcelain layer on the surface of the metal frame 2, a dental prosthesis described later is obtained. Here, an embodiment of the dental metal frame for porcelain bonding is described, but a dental metal frame also includes, for example, a dental prosthesis such as an inlay, a crown, a bridge, a denture, a metal denture base, an implant, an abutment, a fixture, or a screw without porcelain bonding.

In the machining process, any machining tool can be used. Examples of the machining tool include a machining center, a milling tool, a drill press, and a lathe. Among these, a machining tool integrated in a CAM system is preferably used. According to such a machining tool, a model acquired by a CAD system or the like can be accurately reflected in a machining result. Therefore, such a machining tool can contribute to the realization of a dental prosthesis with less sense of discomfort in patients when it is attached.

The blank 1' after the machining process shown in FIGS. 5 and 6 includes a flat plate portion 3 derived from the blank 1, and a metal frame 2 cut out so as to be surrounded by a through-hole 4 formed in this flat plate portion 3. As shown in FIG. 6, the metal frame 2 and the flat plate portion 3 are connected to each other through a narrow connection portion 5, and by cutting this connection portion 5 in the end, the metal frame 2 can be separated from the blank 1' after the machining process.

The metal frame 2 shown in FIG. 7 shows a state after it is separated from the blank 1' after the machining process shown in FIGS. 5 and 6. The shape of the metal frame 2 shown in FIG. 7 is one example, and the metal frame 2 can have various shapes according to the type of the dental prosthesis.

For the obtained metal frame 2, a polishing treatment may be performed as desired. Examples of the polishing treatment include barrel polishing and sand blasting.

Further, for the obtained metal frame 2, a secondary process may be performed as desired. Examples of the secondary process include a machining process such as cutting and grinding, a laser process, an electron beam process, a water jet process, an electrical discharge process, a pressing process, an extrusion process, a rolling process, a forging process, a bending process, a squeezing process, a drawing process, a roll-forming process, and a shearing process.

The thus obtained metal frame 2 has high dimensional accuracy due to the excellent machinability of the blank 1 as described above. Such a metal frame 2 can be attached to an affected part with less sense of discomfort, and thus, a burden on a patient can be minimized, and also when a porcelain layer is provided on the surface of the metal frame 2 as described later, high adhesiveness of the porcelain layer and high aesthetic appearance can be realized.

Further, the metal frame 2 has high corrosion resistance, and therefore has excellent biocompatibility.

Moreover, the metal frame 2 has excellent mechanical properties, and therefore strongly resists deformation due to a biting force, and thus has excellent durability.

After the metal frame 2 is separated from the blank 1' after the machining process, the residual flat plate portion 3 also can be used for machining another metal frame 2, and also can be recycled as a starting material for producing a new blank 1. That is, the residual flat plate portion 3 is melted and powdered by an atomization method or the like, whereby a metal powder (the metal powder for powder metallurgy according to the invention) to be used for the production of the blank 1 is obtained.

Dental Prosthesis

Next, an embodiment of a dental prosthesis according to the invention will be described.

Figure 8:
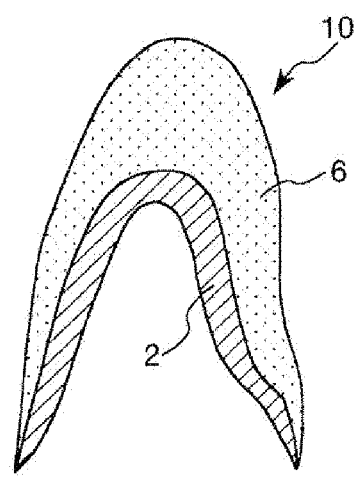
FIG. 8 is a longitudinal cross-sectional view showing an embodiment of a dental prosthesis according to the invention.

FIG. 8 is a longitudinal cross-sectional view showing an embodiment of a dental prosthesis according to the invention.

A dental prosthesis 10 shown in FIG. 8 includes a metal frame 2 and a porcelain layer 6 provided so as to cover a part of the surface of the metal frame 2.

The porcelain layer 6 is a member which plays a part in the aesthetic appearance of the dental prosthesis 10, and generally has a color close to the color of teeth.

Examples of a constituent material of the porcelain layer 6 include a variety of ceramic-based materials such as feldspar, quartz, porcelain clay, and a metal oxide and a variety of resin materials. Among these, from the viewpoint of aesthetic appearance and adhesiveness to the metal frame 2, a ceramic-based material is preferably used. Specific examples thereof include alumina, silica, lithium oxide, sodium oxide, potassium oxide, calcium oxide, iron oxide, magnesia, zirconia, titania, antimony oxide, and cerium oxide, and one type or a mixture of two or more types among these is used.

A slurry containing such a constituent material is applied to the surface of the metal frame 2, followed by a firing treatment, whereby the porcelain layer 6 is formed.

The constituent material of the porcelain layer 6 preferably contains alumina among these. When a ceramic material containing alumina is bonded to the surface of the metal frame 2 by firing, a mullite phase is generated in the vicinity of the boundary surface between the porcelain layer 6 and the metal frame 2. It is considered that this mullite phase is generated by mixing alumina contained in the ceramic material and Si or silicon oxide contained in the metal frame 2. Due to this, the porcelain layer 6 and the metal frame 2 are strongly adhered to each other through the mullite phase so that the porcelain layer 6 strongly resists peeling off, and thus a dental prosthesis having high reliability is obtained. Further, it is considered that due to the generation of the mullite phase, the wettability of the ceramic material to the metal frame 2 is improved during a firing treatment. Accordingly, from such a viewpoint, the adhesiveness of the porcelain layer 6 is considered to be enhanced.

The content of alumina in the constituent material of the porcelain layer 6 is preferably about 2% by mass or more and 50% by mass or less, more preferably about 4% by mass or more and 35% by mass or less, and further more preferably about 6% by mass or more and 25% by mass or less. By setting the content of alumina within the above range, an amount of alumina desired and sufficient for enhancing the adhesiveness between the porcelain layer 6 and the metal frame 2 is ensured, and also the mechanical properties of the porcelain layer 6 itself are enhanced, and thus, a dental prosthesis having higher reliability is obtained.

If the content of alumina is less than the above lower limit, a sufficient amount of the mullite phase is not generated between the porcelain layer 6 and the metal frame 2, and therefore, the wettability of the ceramic material is deteriorated, and thus the adhesiveness of the porcelain layer 6 may be deteriorated. On the other hand, if the content of alumina exceeds the above upper limit, the mechanical properties are liable to be deteriorated (for example, the porcelain layer 6 becomes brittle), and therefore, the adhesiveness of the porcelain layer 6 may be deteriorated just the same.

The average thickness of the porcelain layer 6 is not particularly limited, but is preferably about 0.05 mm or more and 3 mm or less, and more preferably about 0.2 mm or more and 2 mm or less. By setting the average thickness of the porcelain layer 6 within the above range, the adhesiveness of the porcelain layer 6 to the metal frame 2 can be further enhanced.

In the formation of the porcelain layer 6, first, the constituent material of the porcelain layer 6 is finely pulverized by a ball mill, a planetary mill, or the like. Thereafter, according to desire, a heat treatment is performed at about 800° C. or higher and 1100° C. or lower for about 30 minutes or more and 60 minutes or less.

The thus obtained pulverized material is dispersed in a dispersion medium, whereby a material in the form of a slurry or a paste is prepared. In this manner, a slurry or a paste for forming the porcelain layer 6 is obtained. Examples of the dispersion medium include water, propylene glycol, ethylene glycol, glycerin, polymethyl methacrylate, polyvinyl acetate, nitrocellulose, and ethyl cellulose.

The obtained slurry or paste is applied to the surface of the metal frame 2, and a firing treatment is performed. The firing temperature is appropriately set according to the constituent material of the porcelain layer 6, but is set to, for example, 500° C. or higher and 1000° C. or lower. In this manner, a dental prosthesis is obtained.

Hereinabove, the dental blank to be machined, the metal powder for powder metallurgy, the dental metal frame for porcelain bonding, and the dental prosthesis are described with reference to preferred embodiments, however, the invention is not limited thereto.

For example, in the above embodiments, a case where a plurality of dental metal frames for porcelain bonding are cut out from the dental blank to be machined is described. However, the invention is not limited to this case, and can also be applied to a case where one metal frame is cut out from one blank.

EXAMPLES

Next, specific examples of the invention will be described.

1. Production of Dental Blank to be Machined

Sample No. 1

(1) First, a starting material was melted in a high-frequency induction furnace, and then powdered by a spinning water atomization method, whereby a metal powder was obtained. Subsequently, the obtained metal powder was classified using a standard sieve having a mesh size of 150 μm. The alloy composition of the obtained metal powder is shown in Table 1. Incidentally, in the determination of the alloy composition, an optical emission spectrometer for solids (a spark optical emission spectrometer) manufactured by SPECTRO Analytical Instruments GmbH (model: Spectrolab, type: LAVMB08A) was used. Further, in the quantitative analysis of C (carbon), a carbon/sulfur analyzer CS-200 manufactured by LECO Corporation was used.

(2) Subsequently, an organic binder was dissolved in water, whereby a binder solution was prepared. The amount of the organic binder in the binder solution was set to 10 g per kg of the metal powder. Further, the amount of water in the binder solution was set to 50 g per g of the organic binder.

(3) Subsequently, the metal powder was placed in a treatment vessel of a granulating device. Then, the metal powder was tumbled and granulated while spraying the binder solution from a spray nozzle of the granulating device onto the metal powder in the treatment vessel, whereby a granulated powder was obtained.

(4) Subsequently, by using the obtained granulated powder, molding was performed under the following molding conditions, whereby a molded body was obtained.

Molding Conditions:

Molding method: compact-molding

Molding pressure: 300 MPa (3 t/cm$^2$)

(5) Subsequently, the obtained molded body was degreased under the following degreasing conditions, whereby a degreased body was obtained.

Degreasing Conditions

Heating temperature: 470° C.

Heating time: 1 hour

Heating atmosphere: nitrogen atmosphere (6) Subsequently, the obtained degreased body was fired under the following firing conditions, whereby a sintered body was obtained. The obtained dental blank to be machined had a disk shape with a diameter of 100 mm and a thickness of 15 mm.

Firing Conditions

Heating temperature: 1300° C.

Heating time: 3 hours

Heating atmosphere: argon atmosphere

Sample Nos. 2 to 17

Dental blanks to be machined were obtained in the same manner as the sample No. 1 except that those shown in Table 1 were used as the metal powder, respectively.

In Table 1, among the metal powders and the dental blanks to be machined of the respective sample Nos., those corresponding to embodiments of the invention are indicated by "Example", and those not corresponding to the invention are indicated by "Comparative Example".

TABLE 1

| | | Dental blank to be machined | | | | | | | | |
|---|---|---|---|---|---|---|---|---|---|---|
| | | Alloy composition | | | | | | | | |
| | | Cr | Mo | Si | C | Ni | Co | Si/Mo | C/Si | Production method |
| | | % by mass | | | | | | — | — | — |
| Sample No. 1 | Example | 29.0 | 6.04 | 0.70 | 0.05 | 0.01 | remainder | 0.116 | 0.071 | Powder metallurgy |
| Sample No. 2 | Example | 27.4 | 8.53 | 0.95 | 0.04 | 0.01 | remainder | 0.111 | 0.042 | Powder metallurgy |
| Sample No. 3 | Example | 28.3 | 7.24 | 0.86 | 0.05 | 0.01 | remainder | 0.119 | 0.058 | Powder metallurgy |
| Sample No. 4 | Example | 26.2 | 5.3 | 0.52 | 0.02 | 0.01 | remainder | 0.098 | 0.038 | Powder metallurgy |
| Sample No. 5 | Example | 31.8 | 6.54 | 0.75 | 0.07 | 0.01 | remainder | 0.115 | 0.093 | Powder metallurgy |
| Sample No. 6 | Example | 33.4 | 9.25 | 0.64 | 0.12 | 0.01 | remainder | 0.069 | 0.188 | Powder metallurgy |
| Sample No. 7 | Example | 34.6 | 11.5 | 0.94 | 0.31 | 0.01 | remainder | 0.082 | 0.330 | Powder metallurgy |
| Sample No. 8 | Example | 27.2 | 5.52 | 0.97 | 0.08 | 0.01 | remainder | 0.176 | 0.082 | Powder metallurgy |
| Sample No. 9 | Example | 26.5 | 7.79 | 0.83 | 0.15 | 0.02 | remainder | 0.107 | 0.181 | Powder metallurgy |
| Sample No. 10 | Example | 29.8 | 5.87 | 0.65 | 1.24 | 0.02 | remainder | 0.111 | 1.908 | Powder metallurgy |
| Sample No. 11 | Example | 28.6 | 6.12 | 0.74 | 0 | 0.02 | remainder | 0.121 | 0.000 | Powder metallurgy |
| Sample No. 12 | Example | 26.2 | 5.24 | 0.98 | 0.25 | 0.02 | remainder | 0.187 | 0.255 | Powder metallurgy |
| Sample No. 13 | Example | 34.2 | 10.5 | 0.51 | 0.11 | 0.02 | remainder | 0.049 | 0.216 | Powder metallurgy |
| Sample No. 14 | Comparative Example | 29.4 | 5.89 | 0.36 | 0.06 | 0.85 | remainder | 0.061 | 0.167 | Powder metallurgy |
| Sample No. 15 | Comparative Example | 31.6 | 6.74 | 1.26 | 0.06 | 0.77 | remainder | 0.187 | 0.048 | Powder metallurgy |
| Sample No. 16 | Comparative Example | 30.5 | 6.23 | 0.75 | 0.04 | 0.02 | remainder | 0.120 | 0.053 | Casting |
| Sample No. 17 | Comparative Example | 28.4 | 11.6 | 0.87 | 0.11 | 0.89 | remainder | 0.075 | 0.126 | Casting |

2. Evaluation of Dental Blank to be Machined 2.1 Measurement of Total Amount of Si and Content of Si Contained as Silicon Oxide For each of the dental blanks to be machined obtained in the Examples and Comparative Examples, the total amount of Si and the content of Si contained as silicon oxide were measured by gravimetry and ICP optical emission spectroscopy. The measurement results are shown in Table 2.

2.2 Evaluation of Crystal Structure by X-Ray Diffractometry

For each of the dental blanks to be machined obtained in the Examples and Comparative Examples, a crystal structure analysis was performed by X-ray diffractometry. Then, the height and the position of each peak contained in an obtained X-ray diffraction pattern were collated with the database listed in ICDD card, whereby the crystal structure contained in the blank was identified. Then, when the height of the highest peak among the peaks derived from Co was assumed to be 1, the ratio of the height of the highest peak among the peaks derived from $Co_3Mo$ was calculated. The calculation results are shown in Table 2.

2.3 Evaluation of Pore, Dendrite Phase, and Aspect Ratio of Crystal Structure

A test piece was cut out by a machining process from each of the dental blanks to be machined obtained in the Examples and Comparative Examples.

Then, the machined surface of the test piece was polished. Subsequently, the polished surface was observed with a scanning electron microscope, and a region occupied by a pore in the observation image was specified. Then, the average diameter of the region occupied by a pore (this is regarded as the average diameter of a pore) was measured, and also the ratio of the area of the region occupied by a pore to the total area of the observation image (area ratio) was calculated.

Further, by confirming the degree of existence of a dendritic structure in the observation image, the degree of existence of a dendrite phase is evaluated according to the following evaluation criteria.

Evaluation Criteria for Dendrite Phase

A: Almost no dendrite phase exists.

B: A dendrite phase exists in a slight amount (at an area ratio of 10% or less).

C: A dendrite phase exists in a somewhat large amount (at an area ratio of more than 10% and 20% or less).

D: A dendrite phase exists in a large amount (at an area ratio of more than 20%).

Further, the obtained polished surface was observed with a scanning electron microscope, and an average of the aspect ratio of a crystal structure in the observation image was calculated.

The above evaluation results are shown in Table 2.

Figure 9A:
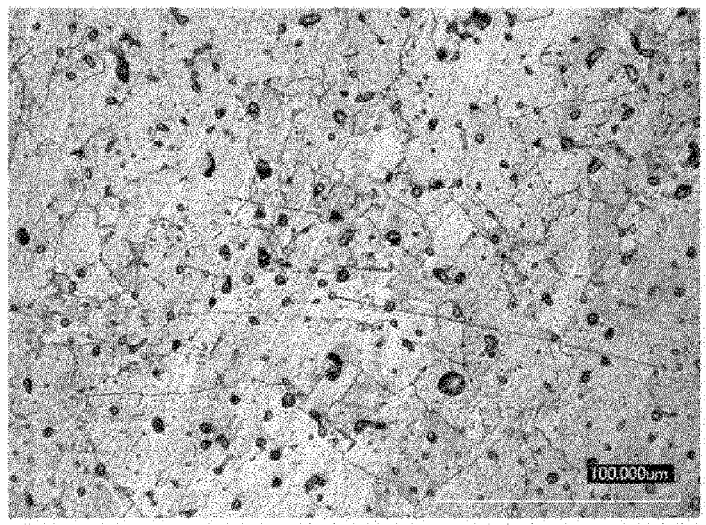
FIGS. 9A and 9B are observation images of dental blanks to be machined obtained in sample No. 1 and sample No. 14, respectively.
Figure 9B:
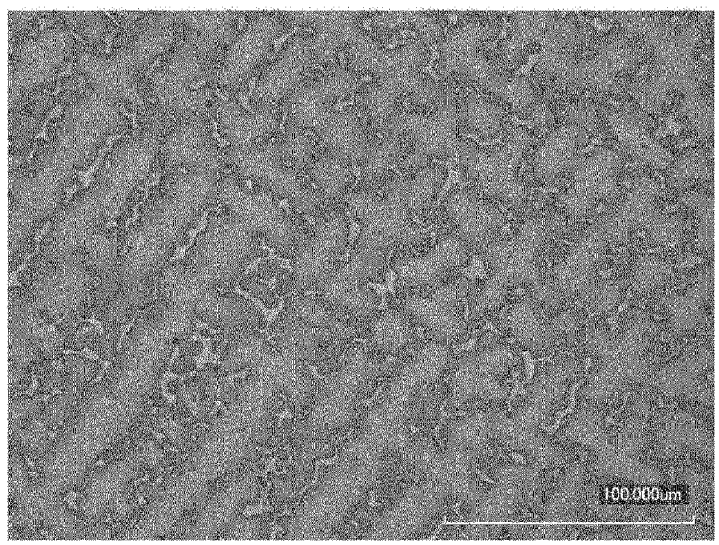

FIGS. 9A and 9B show observation images of the dental blanks to be machined obtained in sample No. 1 and sample No. 14, respectively.

In the observation image of the blank obtained in sample No. 1 (FIG. 9A), the existence of pores substantially uniformly dispersed is confirmed. On the other hand, in the observation image of the blank obtained in sample No. 14 (FIG. 9B), a dendritic structure (dendrite phase) is observed.

Figure 10:
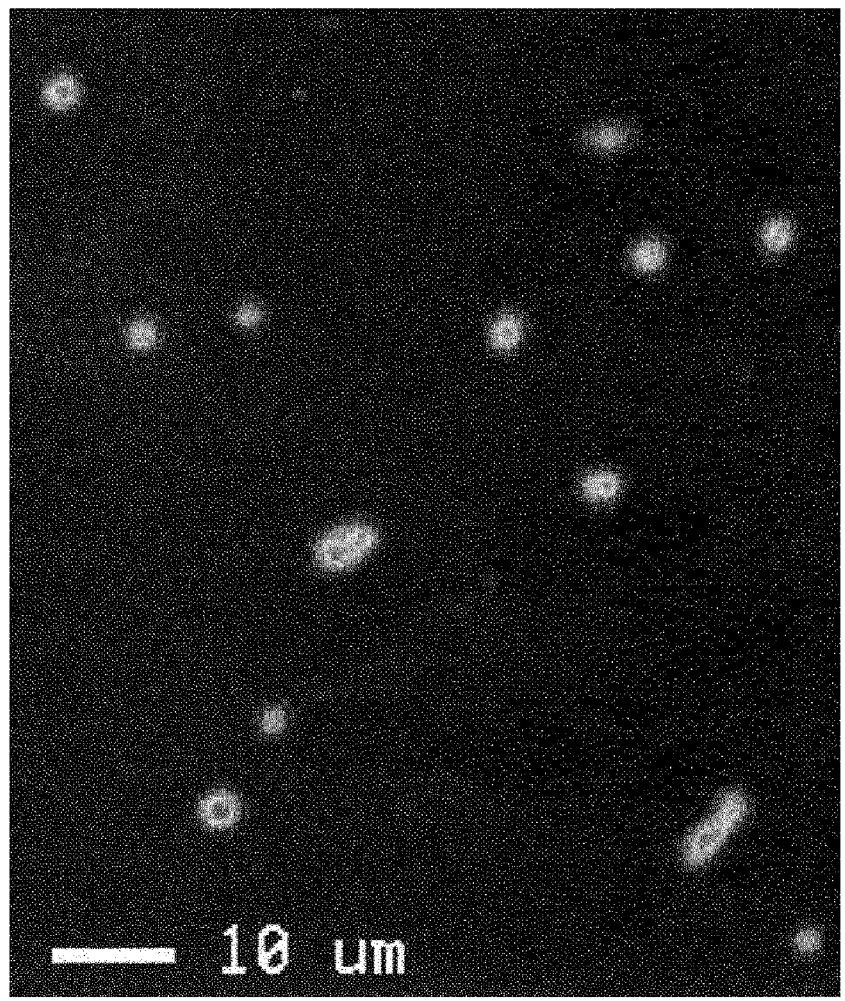
FIG. 10 is a compositional image of Si of the dental blank to be machined obtained in sample No. 1 using an electron beam microanalyzer.

FIG. 10 shows a compositional image of Si of the dental blank to be machined obtained in sample No. 1 using an electron beam microanalyzer.

As apparent from this compositional image, it is confirmed that in the dental blank to be machined obtained in sample No. 1, Si is locally aggregated, and the aggregates (light color portions in FIG. 10) are dispersed. It is considered that this indicates that silicon oxide is segregated at the grain boundary.

2.4 Evaluation of Corrosion Resistance

A test piece was cut out by a machining process from each of the dental blanks to be machined obtained in Examples and Comparative Examples.

Subsequently, for the obtained test pieces, the amount of eluted metal ions was measured in accordance with the test method for corrosion resistance of a noble metal material for dental metal-ceramic restoration specified in JIS T 6118 (2012).

Then, the measurement results were evaluated based on the following evaluation criteria.

Evaluation Criteria for Corrosion Resistance

A: The corrosion resistance is very high (the amount of eluted metal ions is very small).

B: The corrosion resistance is high (the amount of eluted metal ions is small).

C: The corrosion resistance is low (the amount of eluted metal ions is large).

D: The corrosion resistance is very low (the amount of eluted metal ions is very large).

The above evaluation results are shown in Table 2.

the test method for mechanical properties of a noble metal material for dental metal-ceramic restoration specified in JIS T 6118(2012).

Further, the Young's modulus was obtained in accordance with the test method for a dental metal material specified in JIS T 6004(2012).

The measurement results are shown in Table 3.

2.7 Measurement of Fatigue Strength

A test piece was cut out by a machining process from each of the dental blanks to be machined obtained in Examples and Comparative Examples.

Subsequently, for the obtained test pieces, the fatigue strength was measured in accordance with the test method specified in JIS T 0309(2009).

The measurement results are shown in Table 3.

2.8 Evaluation of Machinability

2.8.1 Evaluation Based on Length of Machining Scrap

For each of the dental blanks to be machined obtained in Examples and Comparative Examples, the machinability was evaluated as follows.

First, by using a drill press, a hole is formed in the obtained blank by performing a machining process. Subsequently, machining scraps generated in the machining process were collected, and an average length thereof was determined. Then, the determined average length of the machining scraps was evaluated according to the following evaluation criteria. In the machining process, a drill made of a cemented carbide having a diameter of 2 mm was used, and the rotational speed was set to 420 rpm. Further, a machining oil was not used.

Evaluation Criteria for Machinability

A: The average length of the machining scraps is less than 5 mm (the machinability is particularly favorable).

B: The average length of the machining scraps is 5 mm or more and less than 10 mm (the machinability is favorable).

C: The average length of the machining scraps is 10 mm or more (the machinability is somewhat poor).

TABLE 2

| | | Dental blank to be machined Evaluation results | | | | | | | |
|---|---|---|---|---|---|---|---|---|---|
| | | Ratio of $SiO_2$/ total Si | height of peak in XRD | Pore Average diameter μm | Pore Area ratio % | Dendrite phase | Corrosion resistance | Aspect ratio | Vickers hardness |
| Sample No. 1 | Example | 0.53 | 0.22 | 0.53 | 0.025 | A | A | 0.71 | 350 |
| Sample No. 2 | Example | 0.36 | 0.31 | 0.66 | 0.038 | A | A | 0.69 | 385 |
| Sample No. 3 | Example | 0.45 | 0.27 | 0.58 | 0.032 | A | A | 0.64 | 364 |
| Sample No. 4 | Example | 0.24 | 0.25 | 0.74 | 0.051 | A | B | 0.81 | 401 |
| Sample No. 5 | Example | 0.49 | 0.38 | 0.35 | 0.022 | A | A | 0.75 | 365 |
| Sample No. 6 | Example | 0.32 | 0.42 | 0.89 | 0.087 | A | A | 0.72 | 426 |
| Sample No. 7 | Example | 0.28 | 0.48 | 0.97 | 0.097 | A | A | 0.68 | 448 |
| Sample No. 8 | Example | 0.66 | 0.16 | 0.45 | 0.121 | A | A | 0.83 | 433 |
| Sample No. 9 | Example | 0.77 | 0.36 | 0.43 | 0.112 | A | B | 0.74 | 422 |
| Sample No. 10 | Example | 0.55 | 0.63 | 0.75 | 0.089 | A | B | 0.76 | 449 |
| Sample No. 11 | Example | 0.55 | 0.37 | 0.75 | 0.063 | A | A | 0.59 | 375 |
| Sample No. 12 | Example | 0.84 | 0.08 | 1.28 | 0.256 | A | B | 0.48 | 458 |
| Sample No. 13 | Example | 0.18 | 0.58 | 0.21 | 0.074 | A | A | 0.42 | 486 |
| Sample No. 14 | Comparative Example | 0.06 | 0.76 | 0.25 | 0.087 | B | B | 0.58 | 457 |
| Sample No. 15 | Comparative Example | 0.93 | 0.52 | 0.33 | 0.077 | B | C | 0.36 | 234 |
| Sample No. 16 | Comparative Example | 0.01 | 0.98 | 12.5 | 1.2 | D | C | — | 560 |
| Sample No. 17 | Comparative Example | 0.02 | 1.05 | 10.3 | 1.1 | D | C | — | 620 |

2.5 Measurement of Vickers Hardness

A test piece was cut out by a machining process from each of the dental blanks to be machined obtained in Examples and Comparative Examples.

Subsequently, for the obtained test pieces, the Vickers hardness was measured.

The measurement results are shown in Table 2.

2.6 Measurement of 0.2% Proof Stress, Elongation, and Young's Modulus

A test piece was cut out by a machining process from each of the dental blanks to be machined obtained in Examples and Comparative Examples.

Subsequently, for the obtained test pieces, the 0.2% proof stress and the elongation were measured in accordance with D: The average length of the machining scraps is 10 mm or more and the machining scraps have a spiral shape (the machinability is poor).

The above evaluation results are shown in Table 3.

2.8.2 Evaluation Based on Machining Resistance

For each of the dental blanks to be machined obtained in Examples and Comparative Examples, the machinability was evaluated as follows.

First, the obtained blank was fixed to a measurement section of a three-component tool dynamometer.

Subsequently, a machining process was performed for a surface layer portion of the blank with a machining center such that a processing tool scans along the track shown in FIG. 4A or 4B. Then, among the machining resistances of the three components measured during the machining process, the maximum value was obtained and evaluated according to the following evaluation criteria.

Evaluation Criteria for Machining Resistance

A: The machining resistance is 200 N or less.
B: The machining resistance is more than 200 N and 250 N or less.
C: The machining resistance is more than 250 N and 300 N or less.
D: The machining resistance is more than 300 N.

The above evaluation results are shown in Table 3.

On the other hand, a machining process was performed for an inner layer portion of the blank with a machining center such that a processing tool scans along the track shown in FIG. 4A or 4B. Then, among the machining resistances of the three components measured during the machining process, the maximum value was obtained.

Subsequently, the ratio of the machining resistance in the inner layer portion to the previously obtained machining resistance in the surface layer portion was calculated. The calculated results are shown in Table 3.

As apparent from Tables 2 and 3, it was found that the dental blank to be machined obtained in each Example has excellent corrosion resistance and also has excellent mechanical properties. Further, since the machinability is also excellent, and therefore, it is confirmed that when the blank is subjected to a machining process, the machining resistance is low, and thus, the machining process can be performed smoothly, and a desired shape can be efficiently cut out from the blank. In addition, since it was confirmed that a difference in machining resistance between the inner layer portion and the surface layer portion is sufficiently small, also from this viewpoint, it is confirmed that a desired shape can be efficiently cut out from the dental blank to be machined obtained in each Example.

Further, it was confirmed that the dental blank to be machined obtained in each Example contains a given amount of silicon oxide and pores, but contains almost no dendrite phase.

On the other hand, it was found that the dental blank to be machined obtained in each Comparative Example has low machinability.

3. Production of Dental Prosthesis

A test piece was cut out by a machining process from each of the dental blanks to be machined obtained in Examples and Comparative Examples.

Subsequently, an opaque porcelain paste was applied to the surface of the obtained test piece, followed by firing, whereby a dental prosthesis test piece was obtained.

As the opaque porcelain paste, "Vintage MP" manufactured by Shofu, Inc. was used. Further, the firing temperature was set to 950° C., and this temperature was maintained for 2 minutes. Further, the firing atmosphere was set to be a reduced pressure atmosphere.

TABLE 3

| | | Dental blank to be machined Evaluation results | | | | | | | | |
|---|---|---|---|---|---|---|---|---|---|---|
| | | | | | | Machinability | | Dental prosthesis | | |
| | | 0.2% proof stress MPa | Elongation % | Young's modulus GPa | Fatigue strength MPa | Length of machining scrap | Machining resistance in surface layer portion | Inner layer portion/ surface layer portion % | Composition of porcelain Content of alumina % by mass | Evaluation results Adhesiveness |
| Sample No. 1 | Example | 505 | 35 | >150 | 650 | A | A | 86 | 15 | A |
| Sample No. 2 | Example | 485 | 26 | >150 | 565 | A | A | 95 | 15 | A |
| Sample No. 3 | Example | 501 | 30 | >150 | 675 | A | A | 91 | 15 | A |
| Sample No. 4 | Example | 356 | 10 | >150 | 558 | B | B | 58 | 15 | B |
| Sample No. 5 | Example | 512 | 31 | >150 | 712 | A | A | 89 | 15 | A |
| Sample No. 6 | Example | 512 | 5 | >150 | 683 | A | A | 78 | 15 | A |
| Sample No. 7 | Example | 513 | 4 | >150 | 597 | B | B | 72 | 15 | A |
| Sample No. 8 | Example | 512 | 7 | >150 | 564 | B | B | 121 | 15 | A |
| Sample No. 9 | Example | 507 | 7 | >150 | 625 | A | A | 158 | 15 | A |
| Sample No. 10 | Example | 510 | 4 | >150 | 542 | A | B | 74 | 15 | A |
| Sample No. 11 | Example | 501 | 28 | >150 | 566 | A | B | 76 | 15 | A |
| Sample No. 12 | Example | 563 | 11 | >150 | 485 | A | A | 63 | 15 | A |
| Sample No. 13 | Example | 584 | 6 | >150 | 452 | A | A | 56 | 15 | A |
| Sample No. 14 | Comparative Example | 501 | 4 | — | 486 | D | D | 41 | 15 | D |
| Sample No. 15 | Comparative Example | 276 | 35 | — | 464 | B | B | 215 | 15 | D |
| Sample No. 16 | Comparative Example | 520 | 2 | — | 275 | D | D | 32 | 15 | D |
| Sample No. 17 | Comparative Example | 545 | 1 | — | 246 | D | D | 356 | 15 | D |

4. Evaluation of Dental Prosthesis

With respect to each of the dental prosthesis test pieces obtained using the blanks of Examples and Comparative Examples, a destructive force was applied to each test piece in accordance with the test method for peeling/cracking strength of metal-ceramic dental restorative systems specified in JIS T 6120(2001), and the adhesiveness of the porcelain layer was evaluated according to the following criteria.

Evaluation Criteria in Peeling/Cracking Strength Test

A: The strength is more than twice as large as that of the test piece obtained using the blank of sample No. 14.

B: The strength is more than 1.5 times but not more than twice as large as that of the test piece obtained using the blank of sample No. 14.

C: The strength is more than one time but not more than 1.5 times as large as that of the test piece obtained using the blank of sample No. 14.

D: The strength is not more than one time as large as that of the test piece obtained using the blank of sample No. 14.

The above evaluation results are shown in Table 3.

As apparent from Table 3, it was confirmed that the dental prosthesis obtained using the blank of each Example has higher adhesiveness of the porcelain layer than the dental prosthesis obtained using the blank of each Comparative Example.

Further, each of the dental prosthesis obtained using the blank of each Example was cut, and an area analysis of the cross section was performed using an electron beam microanalyzer. As a result, it was confirmed that mullite exists in layers at the boundary surface between the porcelain layer and the metal frame.

The entire disclosures of Japanese Patent Application Nos. 2013-202722 filed Sep. 27, 2013 and 2014-167734 filed Aug. 20, 2014 are hereby expressly incorporated by reference.

What is claimed is:

1. A dental blank comprising:
    a metal powder sintered body;
    the metal powder sintered body including:
        Co as a main component;
        Cr in a proportion of 26% by mass or more and 35% by mass or less;
        Mo in a proportion of 5% by mass or more and 12% by mass or less; and
        Si in a proportion of 0.5% by mass or more and 1.0% by mass or less,
    wherein a proportion of $Co_3Mo$ in the dental blank is 0.01% by volume or more and 10% by volume or less; and
    wherein an amount of the Si is present as part of a silicon oxide compound and a ratio of the amount of the Si that is part of the silicon oxide relative to the proportion of Si is 10% by mass or more and 90% by mass or less.

2. The dental blank according to claim 1, wherein the silicon oxide is segregated at the grain boundary of the sintered body.

3. The dental blank according to claim 1, wherein in an X-ray diffraction pattern obtained by X-ray diffractometry using a Cu-Kα ray, a ratio of a height of the highest peak among the peaks derived from $Co_3Mo$ identified based on an ICDD card to a height of the highest peak among peaks derived from Co identified based on the ICDD card is 0.01 or more and 0.5 or less.

4. The dental blank according to claim 1, wherein the dental blank has a 0.2% proof stress of 450 MPa or more, an elongation of 2% or more, and a Young's modulus of 150 GPa or more.

5. The dental blank according to claim 1, wherein the dental blank has a Vickers hardness of 200 or more and 480 or less.

6. A metal powder for producing a dental blank, the metal powder comprising:
    Co as a main component;
    Cr in a proportion of 26% by mass or more and 35% by mass or less;
    Mo in a proportion of 5% by mass or more and 12% by mass or less; and
    Si in a proportion of 0.5% by mass or more and 1.0% by mass or less,
    wherein a proportion of $Co_3Mo$ in the metal powder is 0.01% by volume or more and 10% by volume or less; and
    wherein an amount of the Si is present as part of a silicon oxide compound, and a ratio of the amount of the Si that is part of the silicon oxide relative to the proportion of Si is 10% by mass or more and 90% by mass or less.

7. A dental metal frame for bonding to porcelain, the dental metal frame comprises a metal powder sintered body, the dental metal frame comprising:
    Co as a main component;
    Cr in a proportion of 26% by mass or more and 35% by mass or less;
    Mo in a proportion of 5% by mass or more and 12% by mass or less; and
    Si in a proportion of 0.5% by mass or more and 1.0% by mass or less,
    wherein a proportion of $Co_3Mo$ in the dental metal frame is 0.01% by volume or more and 10% by volume or less; and
    wherein an amount of the Si is present as part of a silicon oxide compound, and a ratio of the amount of the Si that is part of the silicon oxide relative to the proportion of Si is 10% by mass or more and 90% by mass or less.

8. The dental metal frame according to claim 7, further comprising:
    a porcelain layer provided on a surface of the dental metal frame.

9. The dental metal frame according to claim 8, wherein the porcelain layer contains alumina, and
    a mullite phase between the dental metal frame and the porcelain layer.

* * * * *